United States Patent
Sharma et al.

(10) Patent No.: US 9,000,150 B2
(45) Date of Patent: Apr. 7, 2015

(54) PROCESS FOR THE PREPARATION OF PURE MEROPENEM TRIHYDRATE

(75) Inventors: Prashant Kumar Sharma, Mohali (IN); Bhupendra Vashishta, Gurgaon (IN); Shailendra K. Singh, Gurgaon (IN); Neera Tiwari, Gurgaon (IN); Subhash Dhar, New Delhi (IN)

(73) Assignee: Ranbaxy Laboratories Limited, New Delhi (IN)

( * ) Notice: Subject to any disclaimer, the term of this patent is extended or adjusted under 35 U.S.C. 154(b) by 89 days.

(21) Appl. No.: 13/880,010

(22) PCT Filed: Oct. 21, 2011

(86) PCT No.: PCT/IB2011/054727
§ 371 (c)(1),
(2), (4) Date: Jun. 13, 2013

(87) PCT Pub. No.: WO2012/052978
PCT Pub. Date: Apr. 26, 2012

(65) Prior Publication Data
US 2013/0253184 A1    Sep. 26, 2013

(30) Foreign Application Priority Data
Oct. 22, 2010  (IN) .......................... 2520/DEL/2010

(51) Int. Cl.
*C07D 477/20*   (2006.01)

(52) U.S. Cl.
CPC .................................. *C07D 477/20* (2013.01)

(58) Field of Classification Search
CPC ....................................................... C07D 477/20
USPC .................................................. 540/302, 350
See application file for complete search history.

(56) References Cited

U.S. PATENT DOCUMENTS 4,888,344 A    12/1989   Sunagawa et al. ............ 514/210

FOREIGN PATENT DOCUMENTS

| WO | WO 2005/118586 | 12/2005 | ........... C07D 477/20 |
| WO | WO 2006/035300 | 4/2006 | ........... C07D 477/20 |
| WO | WO 2007/029084 | 3/2007 | ........... C07D 477/20 |
| WO | WO 2007/104221 | 9/2007 | ........... C07D 477/04 |

OTHER PUBLICATIONS

Lawton, Simon. Organic Process Resaerch & Development 13 (2009) 1357-1363.*
"Pure." Merriam-Webster.com. Merriam-Webster, n.d. Web. Sep. 9, 2014. <http://www.merriam-webster.com/dictionary/pure>.*

* cited by examiner

*Primary Examiner* — Golam M M Shameem
*Assistant Examiner* — Laura Daniel (57) ABSTRACT

The present invention relates to a process for the preparation of pure meropenem trihydrate.

6 Claims, 10 Drawing Sheets

Figure 1

FIGURE 1A: TABLE OF VALUES FOR THE XRPD PATTERN DEPICTED IN FIGURE 1

| Pos [° 2θ] | d-spacing [Å] | Rel. Int [%] |
|---|---|---|
| 11.26 | 7.86 | 18.58 |
| 12.91 | 6.86 | 97.55 |
| 16.58 | 5.35 | 58.33 |
| 16.93 | 5.24 | 100.00 |
| 18.54 | 4.78 | 73.10 |
| 19.15 | 4.63 | 47.27 |
| 19.46 | 4.56 | 12.56 |
| 20.17 | 4.40 | 12.02 |
| 20.47 | 4.33 | 13.39 |
| 21.55 | 4.12 | 17.28 |
| 21.92 | 4.06 | 63.68 |
| 22.09 | 4.02 | 27.22 |
| 22.47 | 3.96 | 63.90 |
| 22.99 | 3.87 | 18.83 |
| 23.49 | 3.79 | 31.41 |
| 25.35 | 3.51 | 38.86 |
| 26.62 | 3.35 | 14.55 |
| 27.06 | 3.30 | 27.83 |
| 28.42 | 3.14 | 27.20 |
| 29.14 | 3.06 | 30.99 |
| 29.68 | 3.01 | 20.15 |
| 29.80 | 3.00 | 10.15 |
| 30.39 | 2.94 | 42.48 |
| 31.20 | 2.86 | 15.74 |
| 31.40 | 2.85 | 14.55 |
| 31.96 | 2.80 | 30.33 |
| 33.75 | 2.65 | 25.71 |
| 34.81 | 2.58 | 24.47 |
| 35.45 | 2.53 | 20.35 |
| 37.94 | 2.37 | 10.30 |
| 39.39 | 2.29 | 26.44 |

Figure 2

FIGURE 2A: TABLE OF VALUES FOR THE XRPD PATTERN DEPICTED IN FIGURE 2

| Pos [° 2θ] | d-spacing [Å] | Rel. Int [%] |
|---|---|---|
| 11.27 | 7.85 | 48.87 |
| 12.91 | 6.86 | 100.00 |
| 16.58 | 5.35 | 39.83 |
| 16.93 | 5.24 | 71.60 |
| 18.54 | 4.79 | 39.15 |
| 19.15 | 4.64 | 72.90 |
| 19.46 | 4.56 | 12.86 |
| 20.17 | 4.40 | 13.97 |
| 20.47 | 4.34 | 12.09 |
| 21.55 | 4.12 | 16.73 |
| 21.91 | 4.06 | 26.64 |
| 22.09 | 4.02 | 24.81 |
| 22.46 | 3.96 | 39.13 |
| 22.98 | 3.87 | 20.03 |
| 23.49 | 3.79 | 41.80 |
| 25.36 | 3.51 | 19.02 |
| 27.06 | 3.30 | 18.34 |
| 28.43 | 3.14 | 20.43 |
| 29.14 | 3.06 | 18.17 |
| 29.71 | 3.00 | 10.59 |
| 30.40 | 2.94 | 21.24 |
| 31.96 | 2.80 | 16.37 |
| 34.81 | 2.58 | 23.27 |
| 35.47 | 2.53 | 10.13 |
| 39.39 | 2.29 | 11.48 |
| 39.50 | 2.29 | 10.51 |

Figure 3

FIGURE 3A: TABLE OF VALUES FOR THE XRPD PATTERN DEPICTED IN FIGURE 3

| Pos [° 2θ] | d-spacing [Å] | Rel. Int [%] |
|---|---|---|
| 11.26 | 7.86 | 93.84 |
| 12.90 | 6.86 | 100.00 |
| 16.56 | 5.35 | 22.79 |
| 16.92 | 5.24 | 39.63 |
| 18.53 | 4.79 | 50.92 |
| 19.13 | 4.64 | 77.81 |
| 19.45 | 4.56 | 13.66 |
| 20.16 | 4.41 | 14.23 |
| 20.45 | 4.34 | 12.41 |
| 21.55 | 4.12 | 27.81 |
| 21.91 | 4.06 | 19.46 |
| 22.08 | 4.03 | 12.63 |
| 22.45 | 3.96 | 42.22 |
| 22.97 | 3.87 | 13.83 |
| 23.48 | 3.79 | 53.70 |
| 27.04 | 3.30 | 10.96 |
| 28.43 | 3.14 | 32.97 |
| 29.14 | 3.06 | 21.54 |
| 29.68 | 3.01 | 15.16 |
| 29.79 | 3.00 | 12.50 |
| 30.39 | 2.94 | 26.26 |
| 34.80 | 2.58 | 33.70 |
| 39.36 | 2.29 | 11.16 |

Figure 4

FIGURE 4A: TABLE OF VALUES FOR THE XRPD PATTERN DEPICTED IN FIGURE 4

| Pos [° 2θ] | d-spacing [Å] | Rel. Int [%] |
|---|---|---|
| 10.81 | 8.19 | 12.36 |
| 11.33 | 7.81 | 49.82 |
| 12.97 | 6.83 | 81.95 |
| 16.63 | 5.33 | 35.86 |
| 16.98 | 5.22 | 53.14 |
| 18.60 | 4.77 | 45.22 |
| 19.21 | 4.62 | 100.00 |
| 19.52 | 4.55 | 10.52 |
| 20.23 | 4.39 | 15.93 |
| 21.62 | 4.11 | 45.84 |
| 21.97 | 4.05 | 21.92 |
| 22.15 | 4.01 | 16.45 |
| 22.52 | 3.95 | 50.85 |
| 23.04 | 3.86 | 19.48 |
| 23.54 | 3.78 | 34.94 |
| 25.40 | 3.51 | 15.60 |
| 27.11 | 3.29 | 16.23 |
| 28.49 | 3.13 | 28.85 |
| 29.19 | 3.06 | 20.18 |
| 30.46 | 2.94 | 20.89 |
| 32.01 | 2.80 | 13.04 |
| 34.86 | 2.57 | 20.18 |

Figure 5

FIGURE 5A: TABLE OF VALUES FOR THE XRPD PATTERN DEPICTED IN FIGURE 5

| Pos [° 2θ] | d-spacing [Å] | Rel. Int [%] |
| --- | --- | --- |
| 10.74 | 8.24 | 12.63 |
| 11.27 | 7.85 | 79.18 |
| 12.90 | 6.86 | 93.52 |
| 16.57 | 5.35 | 31.31 |
| 16.92 | 5.24 | 53.71 |
| 18.53 | 4.79 | 46.14 |
| 19.14 | 4.64 | 100.00 |
| 19.45 | 4.56 | 12.99 |
| 20.16 | 4.41 | 16.00 |
| 20.46 | 4.34 | 12.04 |
| 21.55 | 4.12 | 46.55 |
| 21.90 | 4.06 | 26.65 |
| 22.08 | 4.03 | 16.16 |
| 22.46 | 3.96 | 52.68 |
| 22.97 | 3.87 | 19.21 |
| 23.48 | 3.79 | 45.42 |
| 25.34 | 3.51 | 13.37 |
| 27.05 | 3.30 | 17.18 |
| 28.42 | 3.14 | 39.33 |
| 29.13 | 3.07 | 21.66 |
| 29.71 | 3.00 | 14.12 |
| 29.80 | 3.00 | 13.70 |
| 30.40 | 2.94 | 24.34 |
| 31.95 | 2.80 | 12.95 |
| 34.80 | 2.58 | 26.62 |
| 35.46 | 2.53 | 10.13 |
| 39.39 | 2.29 | 12.08 |
| 39.49 | 2.29 | 11.75 |

PROCESS FOR THE PREPARATION OF PURE MEROPENEM TRIHYDRATE

FIELD OF THE INVENTION

The present invention relates to a process for the preparation of pure meropenem trihydrate.

BACKGROUND OF THE INVENTION (4R,5S,6S)-3-[[(3S,5S)-5-(dimethylcarbamoyl)-3-pyrrolidinyl]thio]-6-[(1R)-1-hydroxyethyl]-4-methyl-7-oxo-1-azabicyclo[3.2.0]hept-2-ene-2-carboxylic acid of Formula I, commonly known as meropenem, is a synthetic, broad-spectrum, carbapenem antibiotic.

FORMULA I

Meropenem is commercially available as a trihydrate. Several processes for the preparation of meropenem and meropenem trihydrate are described in U.S. Pat. No. 4,888,344; WO Nos. 2006/035300; 2007/029084; 2007/104221; and 2005/118586.

Meropenem trihydrate is generally prepared by dissolving crude meropenem in water followed by cooling and adding a water miscible organic solvent such as acetone or isopropanol. This method requires heating of meropenem and water mixture to achieve complete dissolution and subsequent cooling of the solution along with the addition of water-miscible solvents, and optionally seed crystals, to maximize the precipitation or crystallization of meropenem trihydrate. The present inventors have observed that preparation of meropenem trihydrate from crude meropenem on a large scale results in a increased impurity content, specifically relating to meropenemic acid of Formula II and meropenem dimer of Formula III. The presence of impurities also impacts the yield.

Formula II

Formula III

The present inventors have not found that the problems associated with increased impurities, and the corresponding reduced yields, is due to the higher residence time in the batch mode reactors that are commonly employed during the scale-up. In batch mode reactors, the reaction is allowed to proceed for a specified time period after which the mixtures of unreacted materials and/or by-products, along with the desired end product, are withdrawn. After the reactants or starting materials are fed into the batch mode reactor, no further reactants or starting materials are added. The batch mode reactors have more residence time, especially during the heating and subsequent cooling steps. In the case of meropenem, the present inventors have observed that high residence time of meropenem, along with water, leads to decomposition of meropenem and increases impurity formation. On the other hand, the replacement of water with alternate organic solvents, for example, methanol, in which meropenem is freely soluble and does not require a heating step, results in higher residual solvent content.

SUMMARY OF THE INVENTION

In one general aspect, the present invention provides for a process for the preparation of pure meropenem trihydrate, wherein the process includes:
 a) heating crude meropenem to a temperature of about 40° C. or above in water to obtain a solution;
 b) cooling the solution obtained in step a) to a temperature of about 30° C. or below;
 c) treating the solution or partial solution obtained in step b) with a water-miscible organic solvent; and
 d) isolating pure meropenem trihydrate from the mixture thereof,
wherein steps a) and b) are carried out in a continuous mode reactor with a residence time of about 5 minutes or less.

Embodiments of this aspect may include one or more of the following features. For example, step a) may be carried out at a temperature of between about 60° C. to about 75° C. and the quantity of water in step a) is about 5 times to about 20 times the quantity of crude meropenem.

Step b) may be carried out at a temperature of between about 15° C. to about 25° C. The water-miscible organic solvent may be acetone, acetonitrile, tetrahydrofuran, $C_{1-3}$ alkanol, or mixture(s) thereof.

The pure meropenem trihydrate may be isolated from the reaction mixture by filtration, solvent removal, decantation, or a combination thereof.

DETAILED DESCRIPTION OF THE INVENTION

The present invention provides for a process for preparation of pure meropenem trihydrate. The process includes:
a) heating crude meropenem to a temperature of about 40° C. or above in water to obtain a solution;
b) cooling the solution obtained in step a) to a temperature of about 30° C. or below;
c) treating the solution or partial solution obtained in step b) with a water miscible organic solvent; and
d) isolating pure meropenem trihydrate from the mixture thereof,
wherein steps a) and b) are carried out in a continuous mode reactor with a residence time of about 5 minutes or less.

The crude meropenem may be prepared according to the methods described in U.S. Pat. No. 4,888,344; WO Nos. 2006/035300; 2007/029084; 2007/104221; and 2005/118586. The crude meropenem may be in crystalline or amorphous form. The crude meropenem has impurity content of greater than or equal to about 1.0%. The crude meropenem is heated to a temperature of greater than or equal to about 40° C., for example, about 60° C. to about 75° C., in water to obtain a solution by heating. The quantity of water may be present at about 5 times to about 20 times to the quantity of crude meropenem. For example, about 1000 ml of water may be used for about 50 g to about 200 g of crude meropenem.

The solution so obtained is cooled to a temperature of less than or equal to about 30° C., for example, about 15° C. to about 25° C. The above steps are carried out in a continuous mode reactor, for example, a helically coiled reactor, wherein the crude meropenem is continuously fed in, contacted with water and the solution or partial solution so obtained is continuously removed from the reactor. The residence time in the continuous mode reactor is about 5 minutes or less, for example, about 2 minutes to about 3 minutes.

After cooling to less than or equal to about 30° C., the solution or a partial solution so obtained may be transferred to a batch mode reactor, for example, a round bottom flask and optionally subjected to carbon treatment. The solution or partial solution is optionally seeded with crystals of meropenem trihydrate and treated with a water-miscible organic solvent. Seed crystals of meropenem trihydrate can be prepared according to methods described in WO 2006/035300.

The water-miscible organic solvent may be acetone, acetonitrile, tetrahydrofuran, $C_{1-3}$ alkanol, for example, ethanol, isopropanol and 1-propanol, or mixture(s) thereof. The treatment with the water-miscible organic solvent may be carried out at a temperature of about 15° C. or less, for example, about 0° C. to about 10° C. The pure meropenem trihydrate is isolated from the mixture by filtration, solvent removal, decantation, or a combination thereof.

While the present invention has been described in terms of its specific embodiments, certain modifications and equivalents will be apparent to those skilled in the art and are intended to be included within the scope of the present invention.

DETAILED DESCRIPTION OF THE FIGURES

COMPARATIVE EXAMPLE 1

Preparation of Meropenem Trihydrate by Batch Process

Crude meropenem (30 g) (meropenemic acid: 0.37%; meropenem dimer: 0.56%; total impurity content excluding meropenemic acid and meropenem dimer: 0.80%) was dissolved in de-ionized water (450 ml) pre-heated to 68° C. to 70° C. in a round bottom flask. The solution obtained was cooled to 20° C. to 25° C. over 25 minutes to 30 minutes, treated with carbon, filtered and cooled to 5° C. Meropenem trihydrate seed (0.075 g) was added at 5° C. and subjected to aging for 2 hours at 0° C. to 5° C. Acetone (150 ml) was added at −2° C. to 5° C. and the mixture was subjected to aging for further 3 hours at 0° C. to 5° C. The mixture was filtered and washed with acetone (150 ml) and dried for 5 hours to 8 hours at 36° C. to 38° C. under vacuum to obtain the title compound.
Yield: 74%
Meropenemic acid content: 0.234%
Meropenem dimer content: 0.357%
Total impurity content (excluding meropenemic acid and meropenem dimer): 0.106%

COMPARATIVE EXAMPLE 2

Preparation of Meropenem Trihydrate by Batch Process

Crude meropenem (30 g) (meropenemic acid: 0.37%; meropenem dimer: 0.56%; total impurity content excluding meropenemic acid and meropenem dimer: 0.80%) was dissolved in methanol (120 mL) at 10° C. to 15° C. in a round bottom flask. The solution obtained was treated with carbon (10 g), filtered and cooled to about 10° C. to 15° C. followed by addition of meropenem trihydrate seed crystals (0.075 g) at 12° C. Isopropyl alcohol (200 ml) was added at 0° C. to 10° C. and the filtrate was subjected to aging for further 4 hours at 0° C. to 2° C. The mixture was filtered and washed with acetone (60 ml) and dried for 4 hours to 5 hours at 36° C. to 38° C. under vacuum to obtain the title compound.
Yield: 78%
Meropenemic acid content: 0.072%
Meropenem dimer content: 0.094%
Total impurity content (excluding meropenemic acid and meropenem dimer): 0.191%
Methanol content: 1.06%

EXAMPLE 1

Preparation of Pure Meropenem Trihydrate

Figure 1:
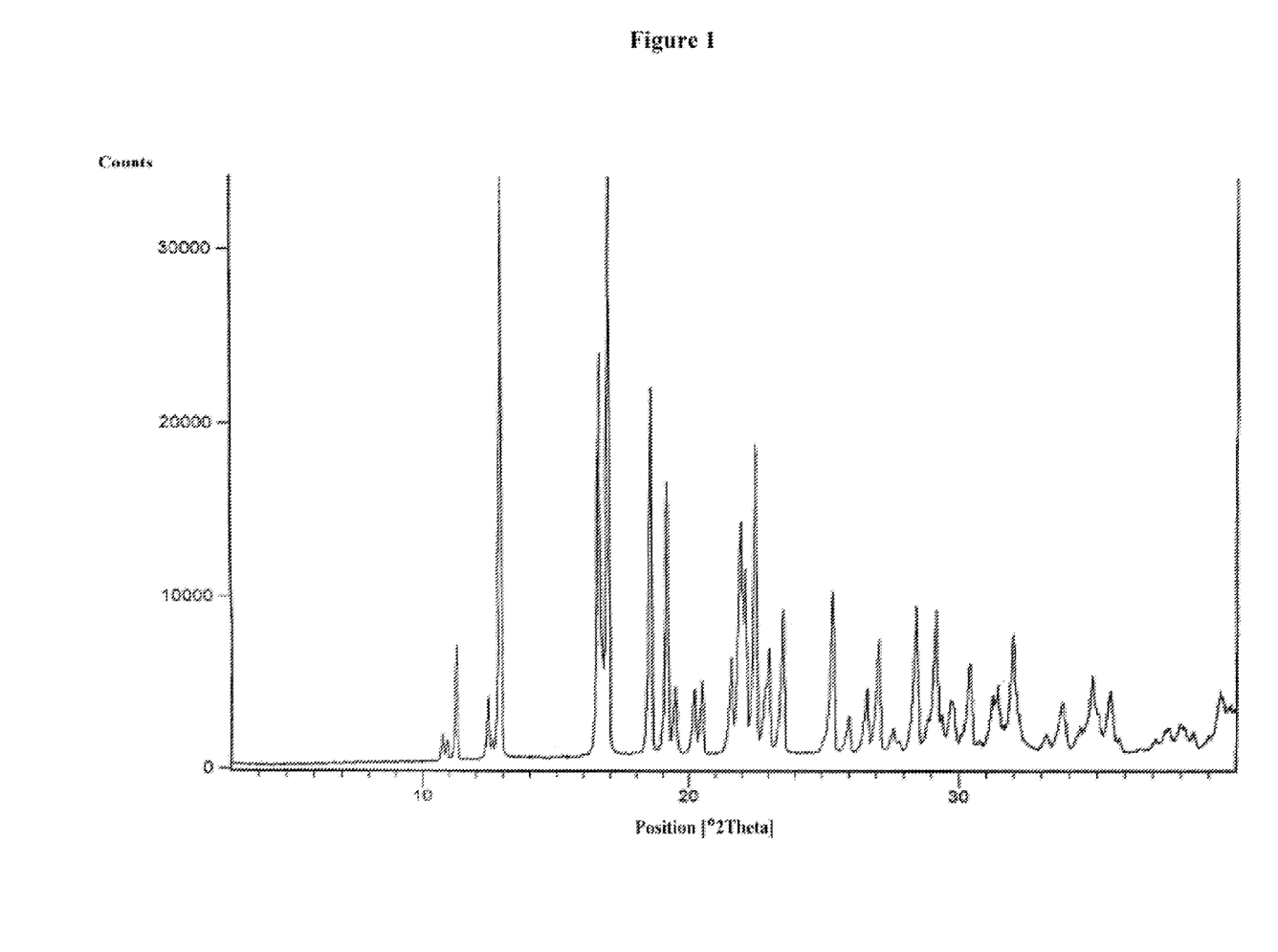
FIG. 1: depicts the XRPD (X-Ray powder diffractogram) of meropenem trihydrate prepared according to Comparative Example 1.
Figure 1A:
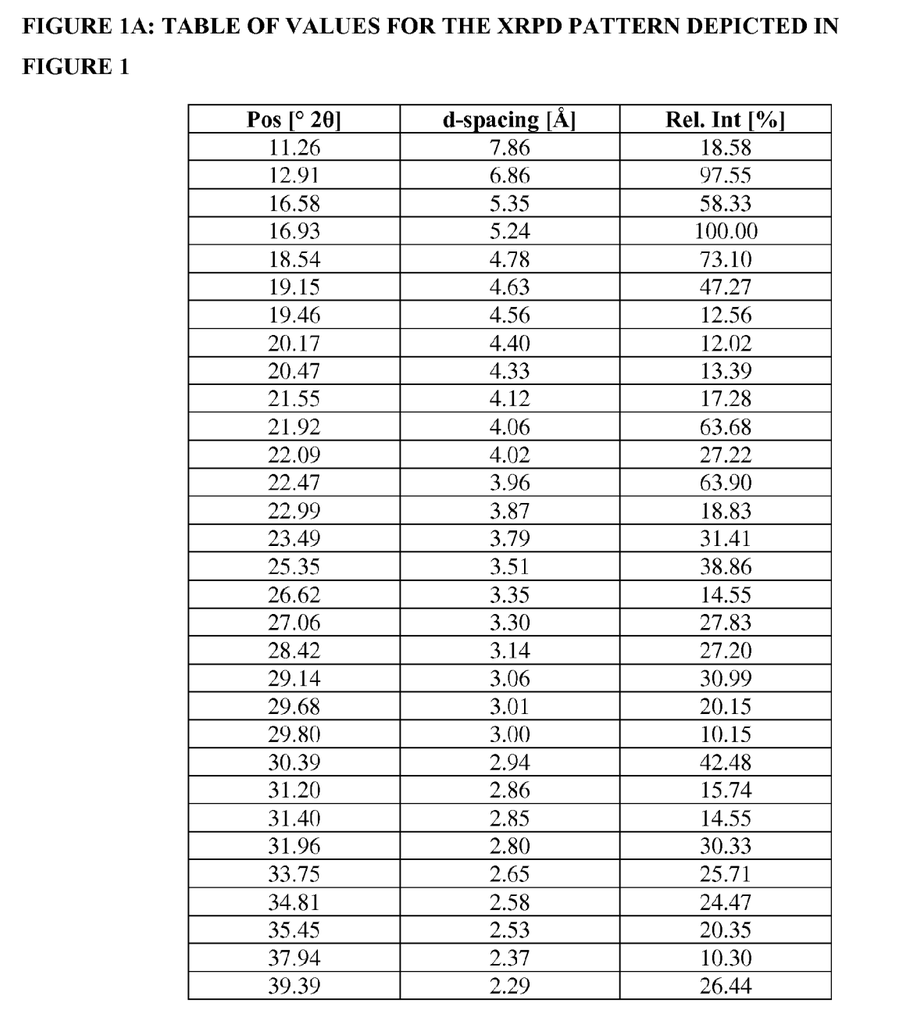
FIG. 1A: Table of values for XRPD pattern depicted in FIG. 1.
Figure 2:
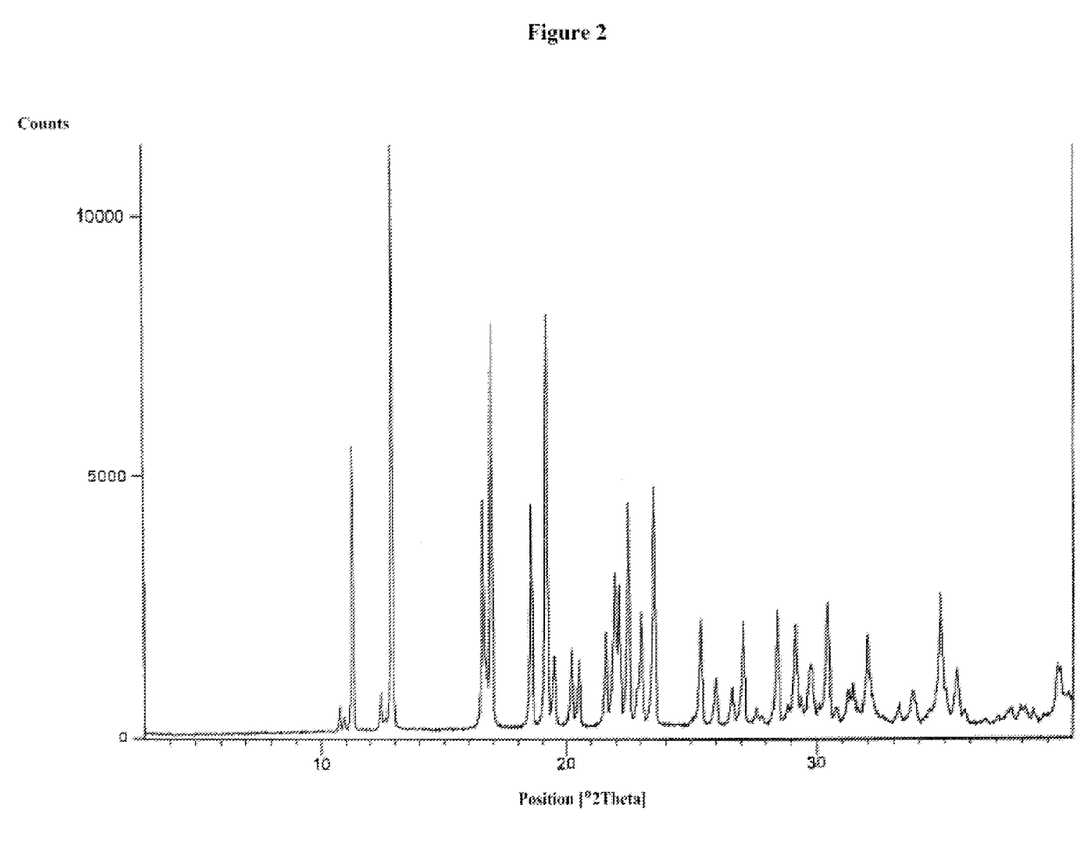
FIG. 2: depicts the XRPD (X-Ray powder diffractogram) of meropenem trihydrate prepared according to Example 1.
Figure 2A:
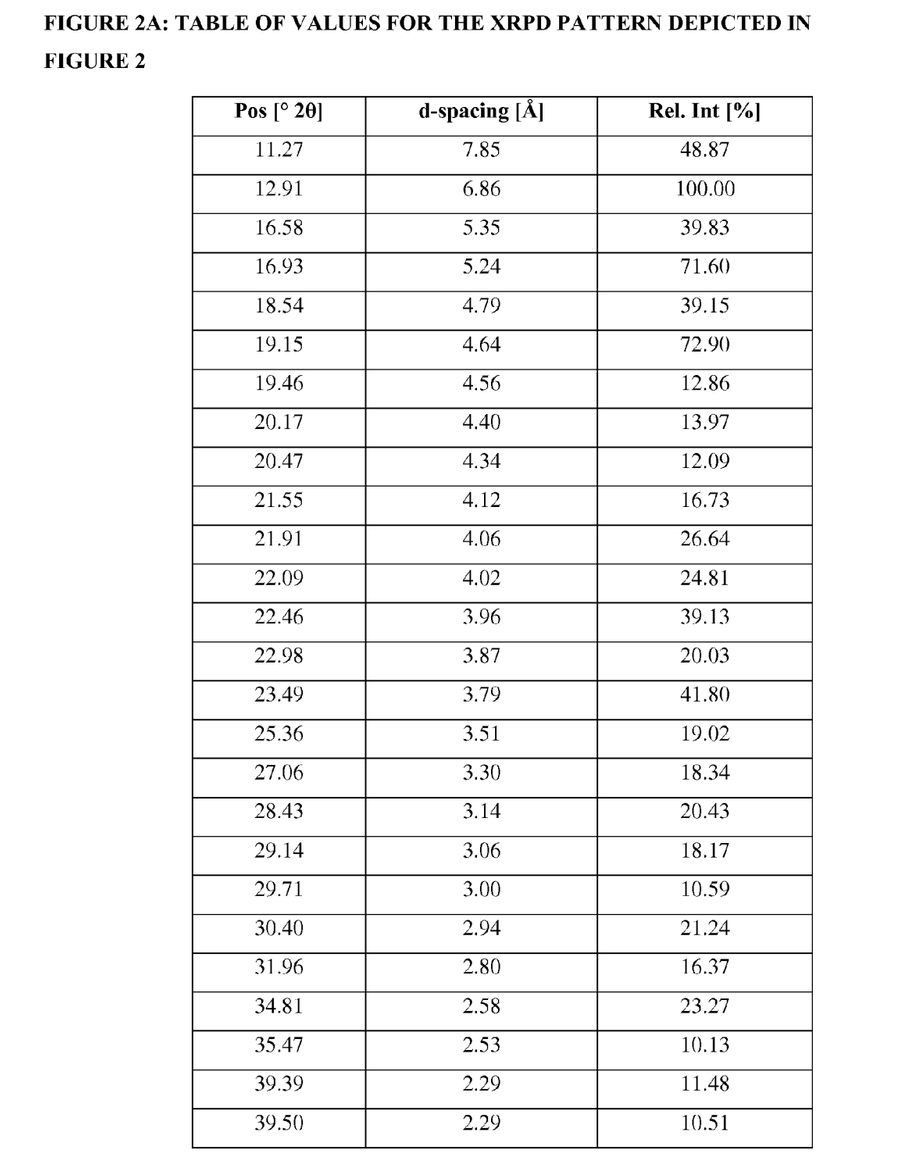
FIG. 2A: Table of values for XRPD pattern depicted in FIG. 2.

Crude meropenem (50 g) (meropenemic acid: 0.37%; meropenem dimer: 0.56%; total impurity content excluding meropenemic acid and meropenem dimer: 0.80%) was dissolved in de-ionized water (700 ml) by heating the mixture to 68° C. and cooled to 20° C. to 25° C. in 2 minutes in a helically coiled reactor. The solution so obtained was treated with carbon (10 g) and filtered. The filtrate obtained was cooled to about 5° C. in a round bottom flask, followed by addition of meropenem trihydrate seed crystals (0.125 g). The mixture was subjected to aging for 2 hours at 0° C. to 5° C. Isopropyl alcohol (500 ml) was added at 0° C. to 5° C. and the mixture was subjected to aging for further 3 hours at 0° C. to 10° C. The mixture was filtered, washed with acetone (150 ml) and dried for 6 hours to 8 hours at 36° C. to 38° C. under vacuum to obtain the title compound having XRPD pattern as depicted in FIG. 2.
Yield: 78%
Meropenemic acid content: 0.017%
Meropenem dimer content: 0.045%
Total impurity content (excluding meropenemic acid and meropenem dimer): 0.074%

EXAMPLE 2

Preparation of Pure Meropenem Trihydrate

Figure 3:
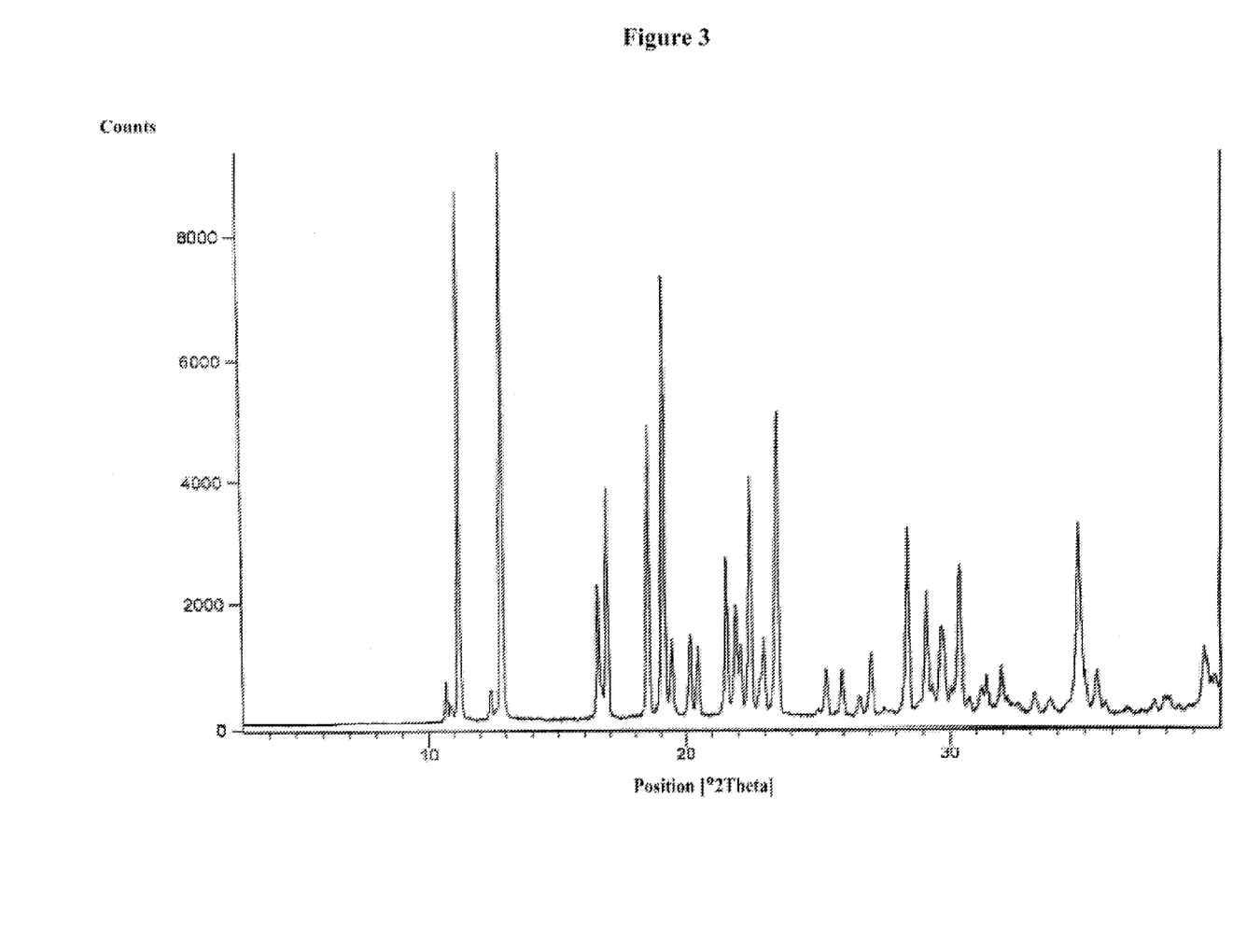
FIG. 3: depicts the XRPD (X-Ray powder diffractogram) of meropenem trihydrate prepared according to Example 2.
Figure 3A:
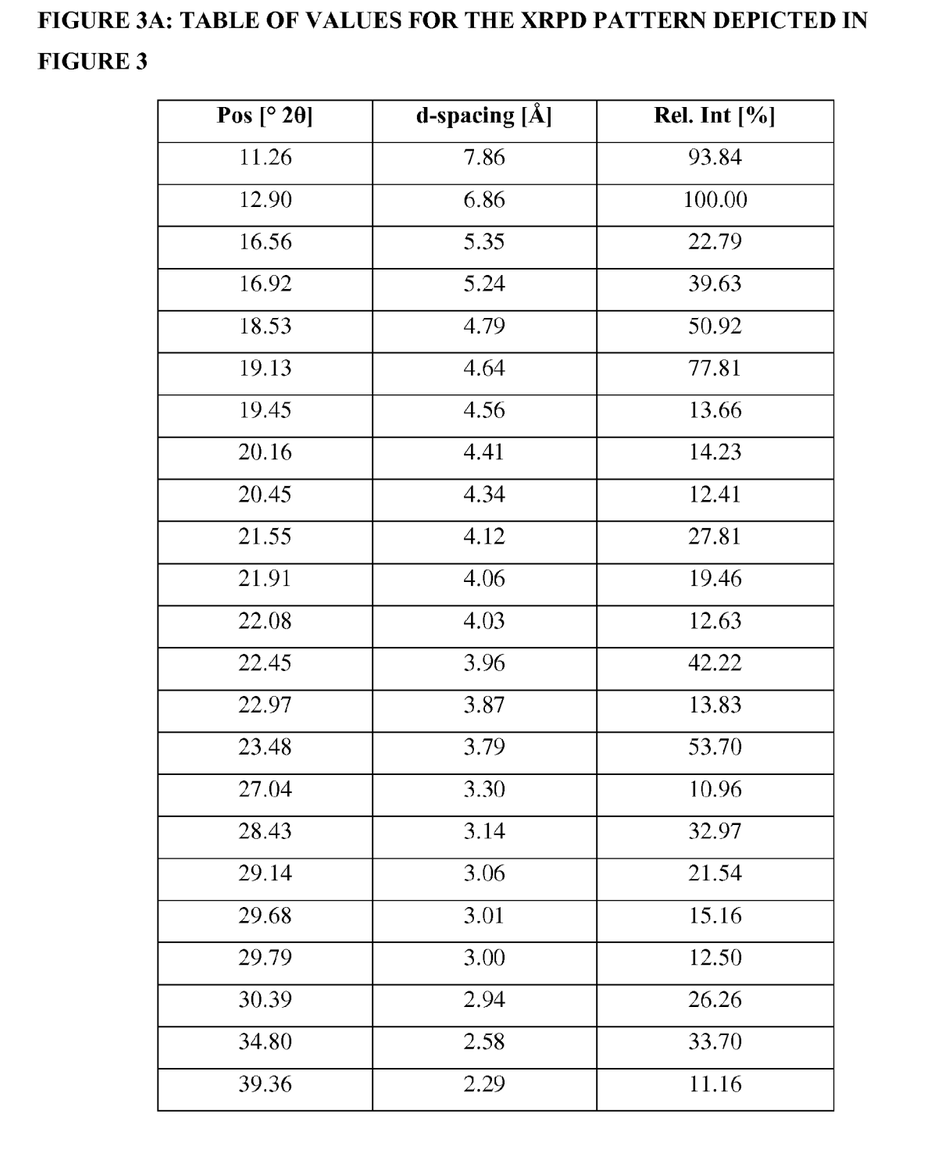
FIG. 3A: Table of values for XRPD pattern depicted in FIG. 3.

Crude meropenem (15 g) (meropenemic acid: 0.37%; meropenem dimer: 0.56%; total impurity content excluding meropenemic acid and meropenem dimer: 0.80%) was dissolved in de-ionized water (210 ml) by heating the mixture to 68° C. and cooled to 20° C. to 25° C. in 2 minutes in a helically coiled reactor. The solution so obtained was treated with carbon (1.5 g) and filtered. The filtrate obtained was cooled to about 5° C. in a round bottom flask, followed by addition of meropenem trihydrate seed crystals (0.0375 g). The mixture was subjected to aging for 2 hours at 0° C. to 5° C. Isopropyl alcohol (500 ml) was added at 0° C. to 5° C. and the mixture was subjected to aging for further 3 hours at 0° C. to 10° C. The mixture was filtered, washed with acetone (150 ml) and dried for 6 hours to 8 hours at 36° C. to 38° C. under vacuum to obtain the title compound having XRPD pattern as depicted in FIG. 3.
Yield: 79%
Meropenemic acid content: 0.056%
Meropenem dimer content: 0.078%
Total impurity content (excluding meropenemic acid and meropenem dimer): 0.181%

EXAMPLE 3

Preparation of Pure Meropenem Trihydrate

Crude meropenem (100 g) (meropenemic acid: 0.37%; meropenem dimer: 0.56%; total impurity content excluding meropenemic acid and meropenem dimer: 0.80%) was dissolved in de-ionized water (1400 ml) by heating the mixture to 68° C. and cooled to 20° C. to 25° C. in 2 minutes in a helically coiled reactor. The solution so obtained was treated with carbon (10 g) and filtered. The filtrate obtained was cooled to about 5° C. in a batch mode reactor (round bottom flask), followed by addition of meropenem trihydrate seed crystals (0.025 g). The mixture was subjected to aging for 2 hours at 0° C. to 5° C. Isopropyl alcohol (500 ml) was added at 0° C. to 5° C. and the mixture was subjected to aging for further 3 hours at 0° C. to 10° C. The mixture was filtered, washed with acetone (150 ml) and dried for 6 hours to 8 hours at 36° C. to 38° C. under vacuum to obtain the title compound.
Yield: 79%
Meropenemic acid content: 0.049%
Meropenem dimer content: 0.050%
Total impurity content (excluding meropenemic acid and meropenem dimer): 0.173%

EXAMPLE 4

Preparation of Pure Meropenem Trihydrate

Step 1:
Crude meropenem (100 g) (meropenemic acid: 0.37%; meropenem dimer: 0.56%; total impurity content excluding meropenemic acid and meropenem dimer: 0.80%) was dissolved in de-ionized water (1400 ml) by heating the mixture to 68° C. and cooled to 20° C. to 25° C. in 2 minutes in a helically coiled reactor. The solution so obtained was treated with carbon (10 g) and filtered.

Figure 4:
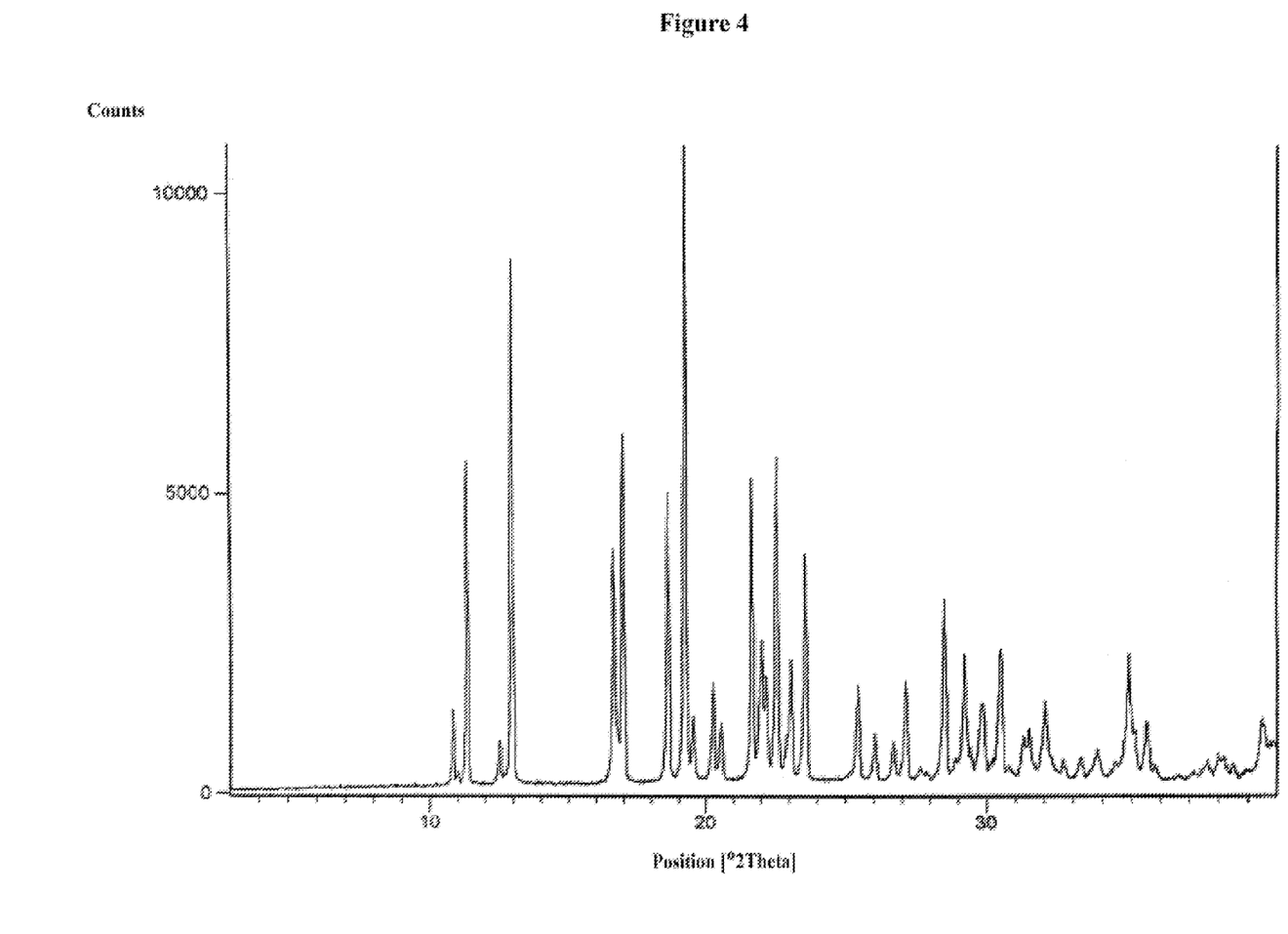
FIG. 4: depicts the XRPD (X-Ray powder diffractogram) of meropenem trihydrate prepared according to Example 4—Part A.
Figure 4A:
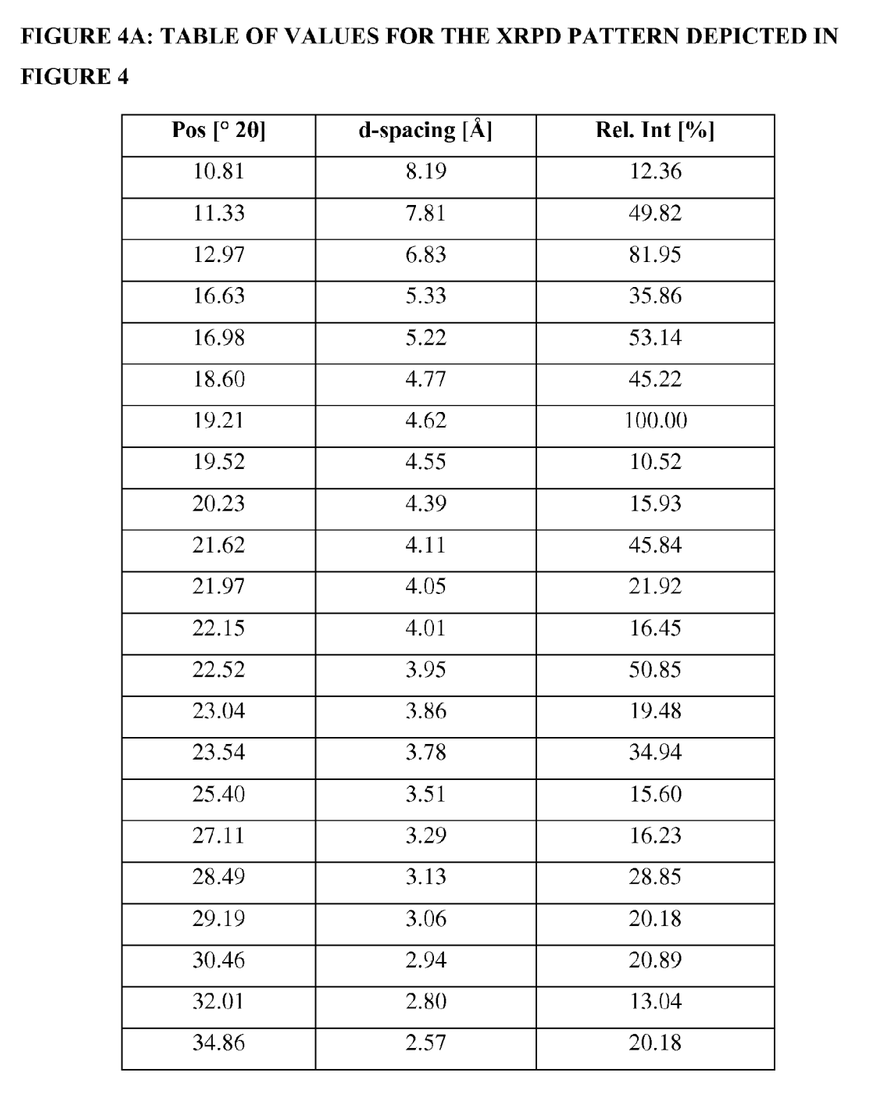
FIG. 4A: Table of values for XRPD pattern depicted in FIG. 4.

Step 2: Part A
Solution equivalent to 25 g of input crude meropenem, obtained according to step 1, was cooled to about 5° C. in a round bottom flask, followed by addition of meropenem trihydrate seed crystals (0.0625 g) at 5° C. The mixture was subjected to aging for 2 hours at 0° C. to 5° C. Mixture of isopropyl alcohol (125 ml) and acetone (125 ml) was added at 0° C. to 10° C. and the mixture was subjected to aging for further 3 hours at 0° C. to 10° C. The mixture was filtered, washed with acetone (75 ml) and dried for 6 hours to 8 hours at 36° C. to 38° C. under vacuum to obtain the title compound having XRPD pattern as depicted in FIG. 4.
Yield: 78%
Meropenemic acid content: 0.031%
Meropenem dimer content: 0.066%
Total impurity content (excluding meropenemic acid and meropenem dimer): 0.122%

Figure 5:
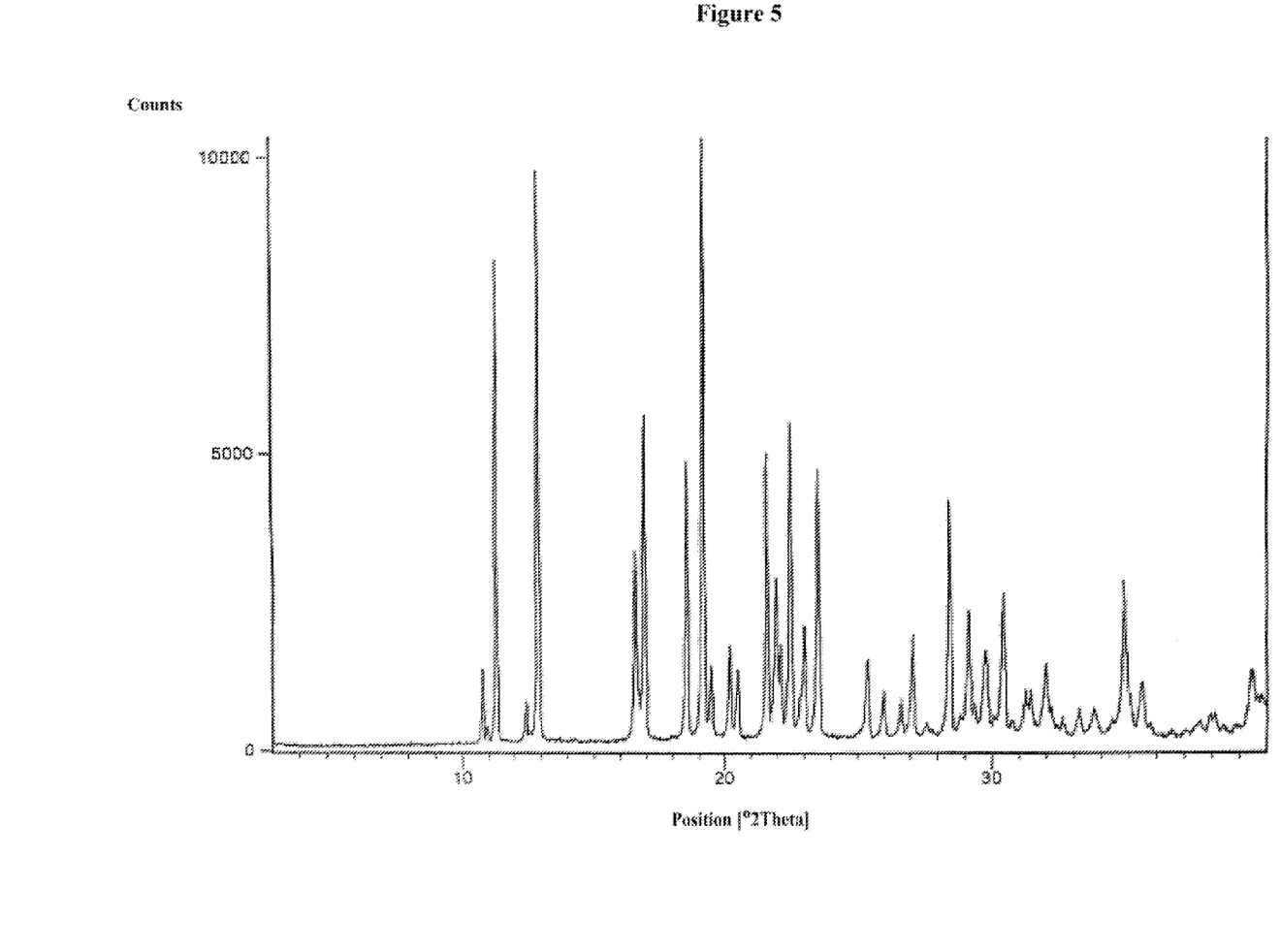
FIG. 5: depicts the XRPD (X-Ray powder diffractogram) of meropenem trihydrate prepared according to Example 4—Part B.
Figure 5A:
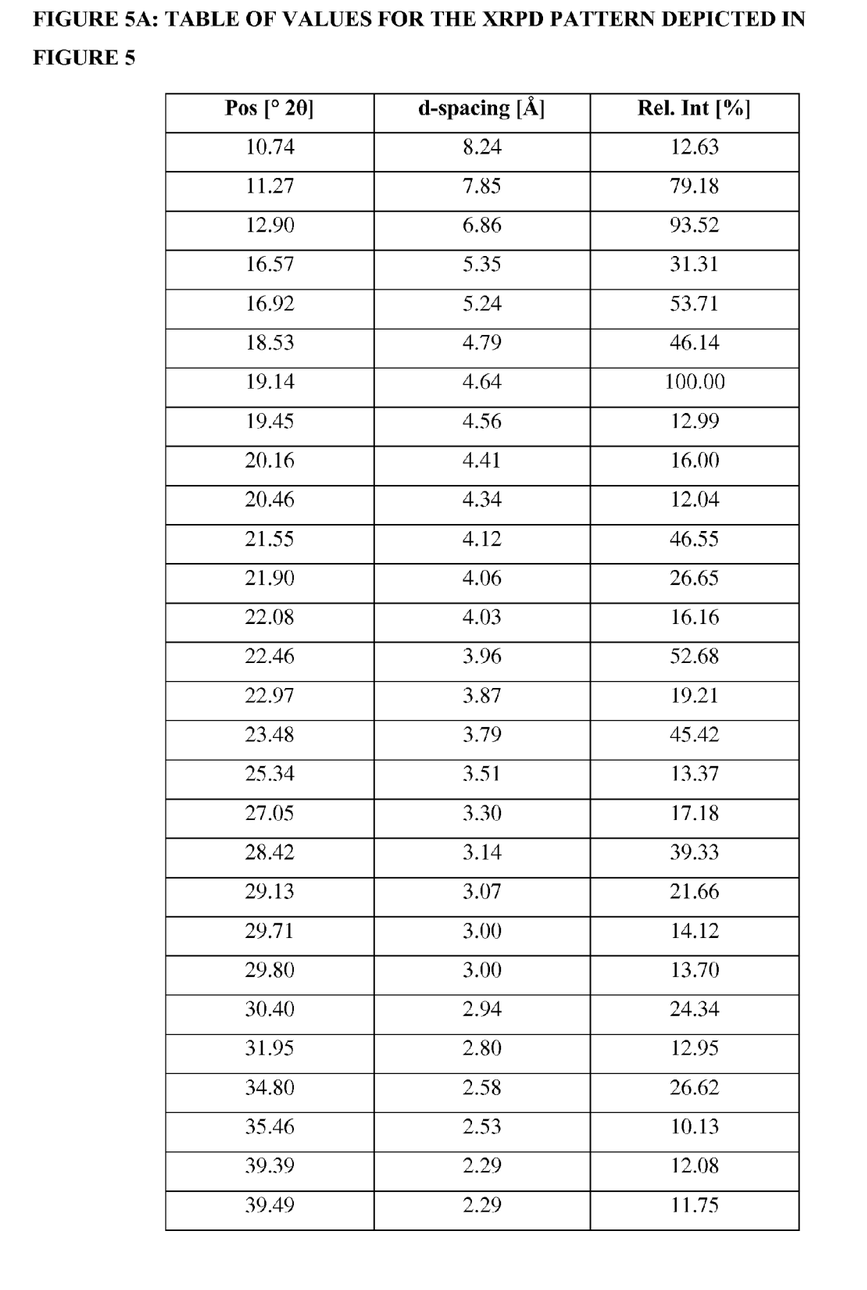
FIG. 5A: Table of values for XRPD pattern depicted in FIG. 5.

Step 2: Part B
Solution equivalent to 25 g of input crude meropenem, obtained according to step 1 was cooled to about 0° C. to 5° C. in a round bottom flask, followed by addition of meropenem trihydrate seed crystals (0.0625 g) at 5° C. The mixture was subjected to aging for 2 hours at 0° C. to 5° C. Acetone (500 ml) was added at 0° C. to 10° C. and the mixture was subjected to aging for further 3 hours at 0° C. to 10° C. The mixture was filtered, washed with acetone (75 ml) and dried for 6 hours to 8 hours at 36° C. to 38° C. under vacuum to obtain the title compound having XRPD pattern as depicted in FIG. 5.
Yield: 80%
Meropenemic acid content: 0.036%
Meropenem dimer content: 0.071%
Total impurity content (excluding meropenemic acid and meropenem dimer): 0.133%.

We claim:
1. A process for the preparation of meropenem trihydrate, wherein the process comprises:
   a) heating crude meropenem to a temperature of 40° C. or above in water to obtain a solution;
   b) cooling the solution obtained in step a) to a temperature of 30° C. or below;
   c) treating the solution or partial solution obtained in step b) with a water-miscible organic solvent; and
   d) isolating meropenem trihydrate from the mixture thereof, wherein steps a) and b) are carried out in a continuous mode reactor with a residence time of 5 minutes or less.

2. The process according to claim 1, wherein step a) is carried out at a temperature of between 60° C. to 75° C.

3. The process according to claim 1, wherein the quantity of water in step a) is 5 times to 20 times to the quantity of crude meropenem.

4. The process according to claim 1, wherein step b) is carried out at a temperature of between 15° C. to 25° C.

5. The process according to claim 1, wherein the water-miscible organic solvent comprises acetone, acetonitrile, tetrahydrofuran, $C_{1-3}$ alkanol, or mixture(s) thereof.

6. The process according to claim 1, wherein the meropenem trihydrate is isolated from the reaction mixture by filtration, solvent removal, decantation, or a combination thereof.

* * * * *